(12) United States Patent
Chen et al.

(10) Patent No.: US 11,134,627 B2
(45) Date of Patent: Oct. 5, 2021

(54) **BREEDING METHOD AND APPLICATION OF NEW DOWNY MILDEW-RESISTANT INTERSPECIFIC HYBRID *CUCUMIS SATIVUS* VARIETY**

(71) Applicant: Nanjing Agricultural University, Jiangsu (CN)

(72) Inventors: Jinfeng Chen, Jiangsu (CN); Ji Li, Jiangsu (CN); Qunfeng Lou, Jiangsu (CN); Chuntao Qian, Jiangsu (CN); Kaijing Zhang, Jiangsu (CN); Chunyan Cheng, Jiangsu (CN); Xiaqing Yu, Jiangsu (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 0 days.

(21) Appl. No.: 16/703,244

(22) Filed: Dec. 4, 2019

(65) Prior Publication Data

US 2020/0196546 A1  Jun. 25, 2020

(30) Foreign Application Priority Data

Dec. 6, 2018  (CN) .......................... 201811487242.2

(51) Int. Cl.
*A01H 1/04* (2006.01)
*A01H 6/34* (2018.01)
*A01H 1/02* (2006.01)
*C12Q 1/6895* (2018.01)

(52) U.S. Cl.
CPC ................ *A01H 1/04* (2013.01); *A01H 1/02* (2013.01); *A01H 6/346* (2018.05); *C12Q 1/6895* (2013.01); *C12Q 2600/13* (2013.01); *C12Q 2600/158* (2013.01)

(58) Field of Classification Search
CPC ..................................................... A01H 1/02
See application file for complete search history.

(56) References Cited

FOREIGN PATENT DOCUMENTS

CN           101785426           7/2010

OTHER PUBLICATIONS

Pang et al 2013 Journal of Phytopathology 161:536-543 (Year: 2013).*
Zhang et al (2018 Theoretical and Applied Genetics 131:2229-2243), provided by Applicant (Year: 2018).*
2007 Chinese Doctoral Dissertation, ISSN # 1674-022X, entitled "Identification and Characterization of a Cucumber Alien Translocation Line CT-01 Possessing Resistance to Downy Mildew", including English Language Abstract.
Zhang, K. et al., "Complete resistance to powdery mildew and partial resistance to downy mildew in a *Cucumis hystrix* introgression line of cucumber were controlled by a co-localized locus", Theoretical and Applied Genetics, vol. 131, 2018, pp. 2229-2243.

* cited by examiner

*Primary Examiner* — Brent T Page
(74) *Attorney, Agent, or Firm* — Gary J. Gershik (57) ABSTRACT

The present invention discloses a breeding method and application of a new downy mildew-resistant interspecific hybrid *Cucumis sativus* variety. The breeding method comprises the following steps: performing hybridization to obtain F1 with the high-generation inbred line CCMC of 'Changchun dense thorn *Cucumis sativus*' as a female parent and a *Cucumis sativus-Cucumis hystrix* introgression line material IL52 as a male parent, selfing the hybrid F1 to obtain F2, and continuously constructing an F6 recombinant inbred line by the single seed transfer method; and by identifying of phenotypes of the recombinant inbred line populations during the natural inoculation of downy mildew at the adult plant stage in the field for 4 years, recombinant individuals with high resistance and good fruit marketability will be screened; and utilizing backcrossing and molecular marker-assisted selection to obtain the individuals as the new downy mildew-resistant interspecific hybrid *Cucumis sativus* variety in which the genotype in the dm5.2 region coincides with the banding pattern of IL52 and the other chromosome regions are the banding pattern of 'Changchun dense thorn *Cucumis sativus*'. The new variety has a high downy mildew-resistant trait, high yield and excellent fruit quality.

5 Claims, 4 Drawing Sheets
Specification includes a Sequence Listing.

SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Primer indel marker

<400> SEQUENCE: 1
ggatcattct cactctcaag cag                                                23

<210> SEQ ID NO 2

```
<211> LENGTH: 23
<212> TYPE: DNA
<213> ORGANISM: Artificial Sequence
<220> FEATURE:
<223> OTHER INFORMATION: Primer indel marker

<400> SEQUENCE: 2
gtttatggtg ggtttaggtg tga                                       23

<210> SEQ ID NO 3
<211> LENGTH: 23
<212> TYPE: DNA
<213> ORGANISM: Artificial Sequence
<220> FEATURE:
<223> OTHER INFORMATION: Primer indel marker

<400> SEQUENCE: 3
gcatatcctc tcaggctacc aat                                       23

<210> SEQ ID NO 4
<211> LENGTH: 25
<212> TYPE: DNA
<213> ORGANISM: Artificial Sequence
<220> FEATURE:
<223> OTHER INFORMATION: Primer indel marker

<400> SEQUENCE: 4
ttttctgcta aaactgaaat ggttc                                     25

<210> SEQ ID NO 5
<211> LENGTH: 23
<212> TYPE: DNA
<213> ORGANISM: Artificial Sequence
<220> FEATURE:
<223> OTHER INFORMATION: Primer indel marker

<400> SEQUENCE: 5
gtcatactgg tgtgatgagc aaa                                       23

<210> SEQ ID NO 6
<211> LENGTH: 28
<212> TYPE: DNA
<213> ORGANISM: Artificial Sequence
<220> FEATURE:
<223> OTHER INFORMATION: Primer indel marker

<400> SEQUENCE: 6
tttttggtta gttttcgtta tatttgaa                                  28
```

BREEDING METHOD AND APPLICATION OF NEW DOWNY MILDEW-RESISTANT INTERSPECIFIC HYBRID *CUCUMIS SATIVUS* VARIETY

CROSS-REFERENCE TO RELATED APPLICATIONS

This application is claiming priority of Chinese Patent Application No. 201811487242.2, filed Dec. 6, 2018, the contents of each of which are hereby incorporated by reference into the application.

REFERENCE TO A SEQUENCE LISTING

This application incorporates-by-reference nucleotide and/or amino acid sequences which are present in the file named "200313 7595 91197 Sequence Listing SC.txt", which is 2 kilobytes in size, and which was created Mar. 13, 2020 in the IBM-PC machine format, having an operating system compatibility with MS-Windows, which is contained in the text file filed Mar. 13,2020 as part of this application.

BACKGROUND

Technical Field

The present invention belongs to the technical field of molecular genetic breeding of vegetables, and relates to a breeding method and application of a new downy mildew-resistant interspecific hybrid *Cucumis sativus* variety.

Related Art

*Cucumis sativus* (*Cucumis sativus* L., 2n=2x=14) is one of the main vegetables cultivated in large areas around the world, and has extremely high social value and economic benefit. *Cucumis sativus* downy mildew is a frequently occurring worldwide disease, as well as one of the main leaf diseases of *Cucumis sativus*. The *Cucumis sativus* downy mildew has the characteristics of short incubation period, frequent secondary infection, high epidemicity, annual occurrence and so on, bringing severe economic loss to *Cucumis sativus* production. The most cost-effective method for preventing and controlling *Cucumis sativus* downy mildew is to breed disease-resistant varieties, so downy mildew-resistant breeding has become one of the main objectives of disease-resistant *Cucumis sativus* breeding.

The genetic base of *Cucumis sativus* is narrow, and lots of important resistance genes are lacked. Therefore, it is very important to expand a cultivated *Cucumis sativus* variety gene pool and discover excellent resistance genes of relative species of *Cucumis sativus*. *Cucumis hystrix* (*Cucumis hystrix* Chakr., 2n=2x=24), which is the only relative wild species for *Cucumis sativus* cultispecies in the *Cucumis sativus* subgenus, has a variety of resistances to downy mildew, southern root-knot nematode, gummy stem blight, blight, etc. By the interspecific hybridization technique, the ordinarily cultivated *Cucumis sativus* CC3 and the *Cucumis hystrix* were hybridized to obtain an interspecific hybrid F1 (2n=2x=19), and chromosome doubling was carried out to obtain an allotetraploid *Cucumis hytivus* (2n=4x=38). The allotetraploid *C. hytivus* serving as a "bridge" was backcrossed and inbred with the cultivated *Cucumis sativus* CC3 to obtain introgression line populations. These interspecific hybrid *Cucumis sativus* populations carry the excellent traits coming from the *Cucumis hystrix*, including downy mildew resistance.

The conventional *Cucumis sativus* breeding methods have defects, such as low target trait transfer efficiency, long period, etc. At present, the identification of phenotypes of downy mildew-resistant *Cucumis sativus* varieties mainly depends on the method of natural inoculation in fields or inoculation at the seedling stage. This method not only takes a long time and needs a large quantity of manpower and material resources, but also is susceptible to outside conditions, the efficiency of phenotype selection is not high, the difficulty of breeding is high, and the bred *Cucumis sativus* varieties have defects, such as unstable downy mildew resistance, susceptibility to cultivation environments, etc. In recent years, with the development of molecular marker technology, many researchers have employed molecular markers closely linked with target trait genes to assist the selection of germplasms. This method is not affected by gene expression or environmental factors, can carry out selection in the early generation, and is easy to operate, greatly increasing the speed and accuracy of selection. Wherein, the InDel (Insertion/Deletion) molecular marker is a marker which is developed based on whole-genome resequencing. With the advantages of wide spread, high density, high stability and high polymorphism in genomes, easiness in detection, codominant inheritance, good repeatability, low requirement on DNA quality and so on, the InDel (Insertion/Deletion) molecular marker can be efficiently and accurately used in the construction of a genetic map, and the molecular marker linked with a target trait is utilized to assist breeding.

SUMMARY

The objective of the present invention is to provide a highly efficient method for transferring a downy mildew-resistant trait to a *Cucumis sativus* interspecific hybrid.

The objective of the present invention is achieved by the following solution:

A breeding method for a new downy mildew-resistant interspecific hybrid *Cucumis sativus* variety comprises the following steps:

(1) performing hybridization to obtain F1 with the high-generation inbred line CCMC of 'Changchun dense thorn *Cucumis sativus*' as a female parent and a *Cucumis sativus*-*Cucumis hystrix* introgression line material 'IL52' as a male parent, selfing the hybrid F1 to obtain F2, and continuously constructing an F6 recombinant inbred line by the single seed descent method; and by identifying of phenotypes of the recombinant inbred line populations during the natural inoculation of downy mildew at the adult plant stage in the field for 4 years, recombinant individuals with high resistance and good fruit marketability will be screened.

(2) Backcrossing and Molecular Marker-Assisted Selection

Utilizing three InDel markers closely linked with the downy mildew-resistant major effect QTLdm5.2 to proceed with genotype screening from the high-resistance individuals screened out, and selecting individuals in which the dm5.2 region is heterozygous and the other chromosome regions approximate the banding pattern of the high-generation inbred line CCMC of 'Changchun dense thorn *Cucumis sativus*'; the primers of the three InDel markers closely linked with the downy mildew-resistant major effect QTLdm5.2 are respectively: 17ID76-F: SEQ ID NO. 1/17ID76-R: SEQ ID NO. 2;17ID129-F: SEQ ID NO.

3/17ID129-R: SEQ ID NO. 4;17ID185-F: SEQ ID NO. 5/17ID185-R: SEQ ID NO. 6; and selecting the recombinant individuals having high downy mildew resistance and according with the aforementioned genotype to perform backcrossing with the high-generation inbred line CCMC of 'Changchun dense thorn *Cucumis sativus*', and from the first backcrossed generation, continuously selecting the individuals in which the dm5.2 region is heterozygous and the other chromosome regions approximate the banding pattern of the high-generation inbred line CCMC of 'Changchun dense thorn *Cucumis sativus*' to perform backcrossing with the high-generation inbred line CCMC of 'Changchun dense thorn *Cucumis sativus*'; after backcrossing for two generations, selecting the individuals in which the dm5.2 region is heterozygous and the other chromosome regions are almost the banding pattern of the high-generation inbred line CCMC of 'Changchun dense thorn *Cucumis sativus*' for selfing, selecting the individuals in which the dm5.2 region is heterozygous for selfing, and ultimately, obtaining the individuals in which the genotype in the dm5.2 region coincides with the banding pattern of 'IL52' and the other chromosome regions are the banding pattern of the high-generation inbred line CCMC of 'Changchun dense thorn *Cucumis sativus*' as the new downy mildew-resistant interspecific hybrid *Cucumis sativus* variety.

Wherein, the new downy mildew-resistant interspecific hybrid *Cucumis sativus* variety has the following characteristics:

the new downy mildew-resistant interspecific hybrid *Cucumis sativus* variety basically has the traits of the high-generation inbred line CCMC of North China type 'Changchun dense thorn *Cucumis sativus*', as well as downy mildew resistance, and is an inbred line;

the new downy mildew-resistant interspecific hybrid *Cucumis sativus* variety is a asubgynoecious, the growth of plants is vigorous, the internode length is 10 cm to 12.5 cm, the stem diameter is 0.6 cm to 0.75 cm, leaves are green, the average maximum leaf area is 23 cm*22 cm, first female flower nodes are seventh to eleventh nodes, a female flower emerges at each following node, commercial *Cucumis sativus* is linear and green with a large number of white thorns, the average *Cucumis sativus* length is 22 cm to 26 cm, the average *Cucumis sativus* diameter is 3 cm to 4 cm, and both main and lateral bines bear *Cucumis sativus*.

As a preference of the method of the present invention, genotype screening described in step (2) is to utilize the primers of the three InDel markers closely linked with the downy mildew-resistant major effect QTLdm5.2 to carry out PCR amplification for the genomic DNA of the high-resistance individuals screened out, and an amplification product undergoes electrophoresis on 6% non-denaturing polyacrylamide gel; single bands with the same size of 107 bp are amplified out of the high-generation inbred line CCMC of 'Changchun dense thorn *Cucumis sativus*' and extremely downy mildew-susceptible RIL individuals by the InDel marker 17ID76, while single bands with the same size of 114 bp are amplified out of 'IL52' and extremely downy mildew-resistant RIL individuals; single bands with the same size of 155 bp are amplified out of the high-generation inbred line CCMC of 'Changchun dense thorn *Cucumis sativus*' and extremely downy mildew-susceptible RIL individuals by the InDel marker 17ID129, while single bands with the same size of 148 bp are amplified out of 'IL52' and extremely downy mildew-resistant RIL individuals; and single bands with the same size of 97 bp are amplified out of the high-generation inbred line CCMC of 'Changchun dense thorn *Cucumis sativus*' and extremely downy mildew-susceptible RIL individuals by the InDel marker 17ID185, while single bands with the same size of 100 bp are amplified out of 'IL52' and extremely downy mildew-resistant RIL individuals.

As a preference of the method of the present invention, the composition of the PCR amplification reaction system is as follows: 10.0 μL of 2×Taq Master Mix, 4.0 μL of ddH$_2$O, 2.0 mL of forward primer, 2.0 mL of reverse primer, 2.0 mL of DNA (10 ng/uL), and 20 μL of total reaction volume. The reaction procedure is: 5 min of pre-denaturation under 94° C.; 30 s of pre-denaturation under 94° C. in each cycle, 30 s of annealing under 55° C., 1 min of extension under 72° C., and 35 cycles in total; 10 min of extension under 72° C., and storage under 4° C.

The three InDel molecular markers closely linked with the downy mildew-resistant major effect locus which are used for breeding the new downy mildew-resistant interspecific hybrid *Cucumis sativus* variety come from the *Cucumis sativus*-*Cucumis hystrix* introgression line material IL52, and the primers of the InDel molecular markers are as follows: the primers of the molecular marker 17ID76 are 17ID76-F: SEQ ID NO. 1/17ID76-R: SEQ ID NO. 2; the primers of the molecular marker 17ID129 are 17ID129-F: SEQ ID NO. 3/17ID129-R: SEQ ID NO. 4; the primers of the molecular marker 17ID185 are 17ID185-F: SEQ ID NO. 5/17ID185-R: SEQ ID NO. 6.

The present invention discloses application of the three InDel molecular markers closely linked with the downy mildew-resistant major effect locus in the breeding of the new downy mildew-resistant interspecific hybrid *Cucumis sativus* variety.

The primers of the InDel molecular markers closely linked with the downy mildew-resistant major effect locus according to the present invention are selected from any one following pair of primers: the primers of the molecular marker 17ID76 are 17ID76-F: SEQ ID NO. 1/17ID76-R: SEQ ID NO. 2; the primers of the molecular marker 17ID129 are 17ID129-F: SEQ ID NO. 3/17ID129-R: SEQ ID NO. 4; and the primers of the molecular marker 17ID185 are 17ID185-F: SEQ ID NO. 5/17ID185-R: SEQ ID NO. 6.

The present invention discloses application of the primers of the InDel molecular markers closely linked with the downy mildew-resistant major effect locus in the breeding of the new downy mildew-resistant interspecific hybrid *Cucumis sativus* variety.

The present invention discloses application of the new downy mildew-resistant interspecific hybrid *Cucumis sativus* variety bred by the breeding method in the breeding of downy mildew-resistant *Cucumis sativus* hybrids.

In a preferred embodiment of the present invention, the new downy mildew-resistant interspecific hybrid *Cucumis sativus* variety bred by the breeding method according to the present invention and an ordinarily cultivated *Cucumis sativus* with high combining ability are planted according to 3:1, and routine plant management is carried out; bagging treatment is performed at the flowering stage to prevent pollen contamination, and with the new downy mildew-resistant interspecific hybrid *Cucumis sativus* variety as a female parent and the ordinarily cultivated *Cucumis sativus* as a male parent, artificial pollination is performed; mature fruits on the plants of the new downy mildew-resistant interspecific hybrid *Cucumis sativus* variety are harvested, the *Cucumis sativus* are cut open, the seeds are washed and sun-dried, and thereby obtaining downy mildew-resistant first-generation hybrid seeds.

Beneficial Effects:

(1) The new downy mildew-resistant variety in the present patent is bred by the *Cucumis sativus* interspecific hybridization technology, transferring the downy mildew resistance of *Cucumis hystrix* as a wild relative species into an ordinarily cultivated *Cucumis sativus* variety, and the breeding technology for the new downy mildew-resistant interspecific hybrid *Cucumis sativus* variety is created for the first time in the world, and can accelerate the breeding progress of downy mildew resistance of *Cucumis sativus*.

(2) By utilizing the three molecular markers closely linked with the downy mildew-resistant major effect QTL of the *Cucumis sativus-Cucumis hystrix* introgression line in the present invention, the efficiency of selecting downy mildew-resistant loci in sixteen extremely downy mildew-resistant individuals and sixteen extremely downy mildew-susceptible individuals in the RIL population is 100%, and these three molecular markers can be used as linked markers for identifying IL52-based downy mildew-resistant varieties, thus increasing the breeding efficiency.

(3) The new highly downy mildew-resistant interspecific hybrid *Cucumis sativus* variety in the present patent, which is a North China type inbred line *Cucumis sativus* variety, has high yield and excellent fruit quality, and can be directly used as a founder parent for improving other downy mildew-resistant varieties.

DETAILED DESCRIPTION

Unless otherwise specified, the experimental methods used in the following embodiment are conventional methods.

Unless otherwise specified, the materials, reagents and so on used in the following embodiment are commercially available.

By illustrating the specific implementation process of the present invention, those skilled in the art can carry out the present invention according to the specific implementation process without creative work, and the definition of the embodiment should not be deemed as a limitation for the protection scope of the inventor.

Embodiment 1

The breeding and application of a new downy mildew-resistant interspecific hybrid *Cucumis sativus* variety DMR114, including:

1. Traits of Parents:

(1) Downy Mildew Resistance Donor Parent IL52

IL52 (Zhang K, Wang X, Zhu W, et al. Complete resistance to powdery mildew and partial resistance to downy mildew in a *Cucumis hystrix*, introgression line of cucumber were controlled by a co-localized locus[J]. Theoretical & Applied Genetics, 2018,131:2229-2243.) is one of *Cucumis sativus-Cucumis hystrix* introgression line materials, the growth of plants is vigorous, lateral branches are more, fruits are mainly born on lateral bines, the shape of commercial *Cucumis sativus* is elliptic, and the downy mildew resistance is high.

(2) High-Generation Inbred Line CCMC of North China Ecotype Receptor Parent—'Changchun Dense Thorn *Cucumis sativus*'

The high-generation inbred line CCMC of 'Changchun dense thorn *Cucumis sativus*' (recorded in Guan Wei, Zhang Yunxia, Yang Shugiong, Chen Jinfeng, Lou Qunfeng; Creation of *Cucumis Sativus* Ploidy Materials and FISH Identification for Chromosome Composition [J]. Agricultural Sciences in China, 2014,47(17):3513-3522; and Zhang K, Wang X, Zhu W, et al. Complete resistance to powdery mildew and partial resistance to downy mildew in a *Cucumis hystrix*, introgression line of cucumber were controlled by a co-localized locus[J]. Theoretical & Applied Genetics, 2018, 131:2229-2243.) is an inbred line which was obtained by the multi-generation selfing of the North China type table F1 variety—'Changchun dense thorn *Cucumis sativus*', the growth of plants is vigorous, lateral branches are less, fruits are mainly born on main bines, commercial *Cucumis sativus* is shaped like rods, but is susceptible to downy mildew.

2. Specific Transfer and Selection Process of Downy Mildew-Resistant Gene (1) Transfer of Downy Mildew-Resistant Gene The high-generation inbred line CCMC of downy mildew-susceptible 'Changchun dense thorn *Cucumis sativus*' and the downy mildew-resistant *Cucumis sativus-Cucumis hystrix* introgression line 'IL52' were simultaneously subjected to seed soaking, germination acceleration, seeding, field planting and routine plant management.

At the flowering stage, 'Changchun dense thorn *Cucumis sativus*' serving as a female parent and IL52 serving as a male parent were hybridized to obtain F1. The specific operation was as follows: in the afternoon of the day before pollination, the female flower buds of the high-generation inbred line CCMC of 'Changchun dense thorn *Cucumis sativus*' and the male flower buds of 'IL52' which will bloom the next day were wrapped to be isolated; at 8:00 a.m. on the day of blooming, the male flower pollen of 'IL52' was transferred onto the female flower stigmas of the high-generation inbred line CCMC of 'Changchun dense thorn *Cucumis sativus*', one female flower was pollinated by three male flowers, and the pollinated female flowers continued to be wrapped for isolation for three days.

The hybrid F1 was inbred to obtain F2, and a set of F6 recombinant inbred line containing 155 strains continued to be constructed by the single seed descent method. By identifying of phenotypes of the recombinant inbred line populations during the natural inoculation of downy mildew at the adult plant stage in the field for 3 years, recombinant individuals with high resistance and good fruit marketability were screened out.

(2) Backcrossing and Molecular Marker-Assisted Selection

Three InDel markers closely linked with the downy mildew-resistant major effect QTLdm5.2 were utilized to proceed with genotype screening from the high-resistance individuals screened out, and individuals in which the dm5.2 region was heterozygous and the other chromosome regions approximated the banding pattern of the high-generation inbred line CCMC of 'Changchun dense thorn *Cucumis sativus*' were selected. The individuals were highly downy mildew-resistant, lateral branches were more, commercial *Cucumis sativus* was shaped like a cylinder, and the individuals can be subsequently backcrossed with 'Changchun dense thorn *Cucumis sativus*' to obtain a variety with the phenotype of the high-generation inbred line CCMC of 'Changchun dense thorn *Cucumis sativus*' and downy mildew resistance.

The composition of the PCR amplification reaction system for genotype screening by the molecular markers was as follows: 10.0 μL of 2×Taq Master Mix, 4.0 μL of ddH$_2$O, 2.04, of forward primer, 2.0 μL of reverse primer, 2.0 μL of DNA (10 ng/uL), and 20 μL of total reaction volume. The reaction procedure was: 5 min of pre-denaturation under 94° C.; 30 s of pre-denaturation under 94° C. in each cycle, 30 s of annealing under 55° C., 1 min of extension under 72° C., and 35 cycles in total; 10 min of extension under 72° C., and storage under 4° C.

Figure 1:
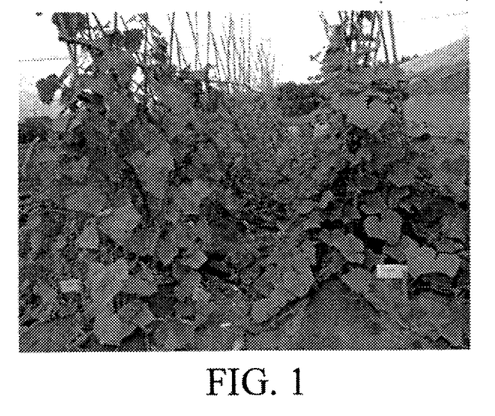
FIG. 1: Downy mildew resistance performance of a downy mildew-susceptible variety (the plant on the left) and a downy mildew-resistant *Cucumis sativus-Cucumis hystrix* introgression line 'IL52' (the plant on the right) under the circumstance of natural inoculation at the adult plant stage in the field
Figure 2:
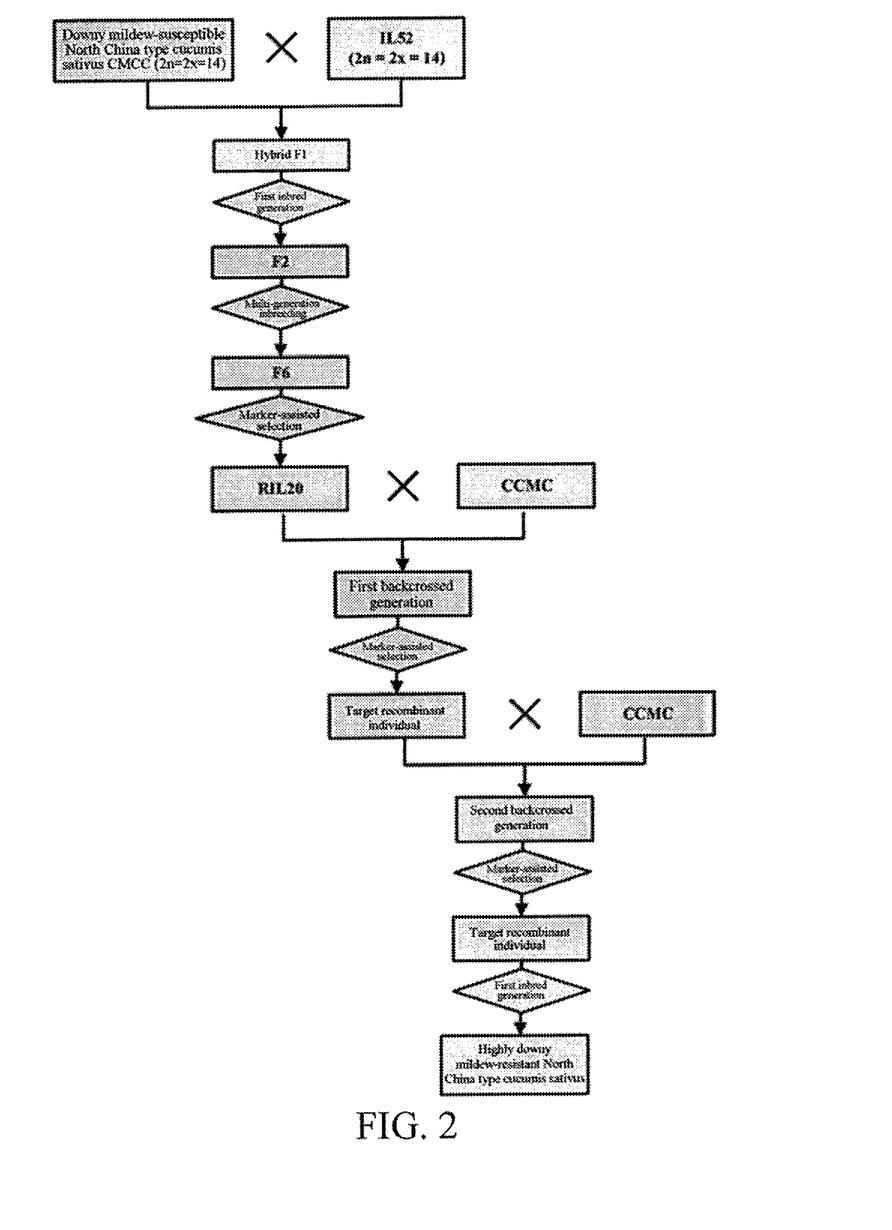
FIG. 2: A technical breeding route for a new downy mildew-resistant interspecific hybrid *Cucumis sativus* variety
Figure 3:
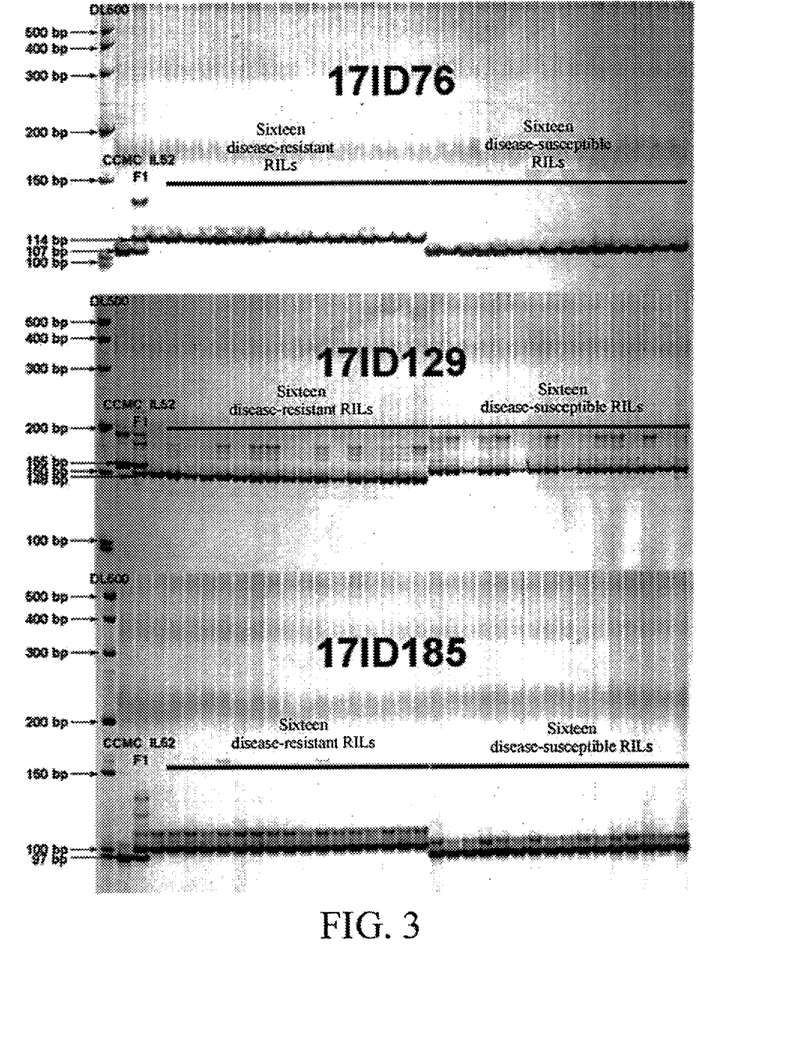
FIG. 3: A verification result of molecular markers in parents, F1 and extremely downy mildew-resistant and extremely downy mildew-susceptible individuals in populations screened out for breeding
Figure 4:
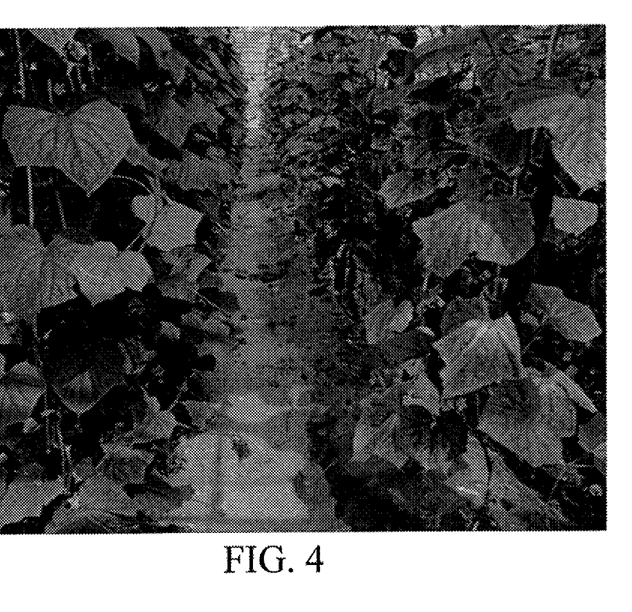
FIG. 4: Resistance performance of a new variety DMR114 (the plant on the left) and a downy mildew-susceptible control (the plant on the right) under the circumstance of natural inoculation of downy mildew in the field

PCR product detection: 1.5 μL of sample was taken from the amplification product and subjected to electrophoresis on 6% non-denaturing polyacrylamide gel; electrodes were electrified, electrophoresis was performed under the constant voltage of 120V for 1.5 hours, then the power was switched off; the gel was taken off, and a silver staining result showed that single bands with the same size of 107 bp were amplified out of the high-generation inbred line CCMC of 'Changchun dense thorn *Cucumis sativus*' and extremely downy mildew-susceptible RIL individuals by the InDel marker 17ID76, while single bands with the same size of 114 bp were amplified out of 'IL52' and extremely downy mildew-resistant RIL individuals; single bands with the same size of 155 bp were amplified out of the high-generation inbred line CCMC of 'Changchun dense thorn *Cucumis sativus*' and extremely downy mildew-susceptible RIL individuals by the InDel marker 17ID129, while single bands with the same size of 148 bp were amplified out of 'IL52' and extremely downy mildew-resistant RIL individuals; and single bands with the same size of 97 bp were amplified out of the high-generation inbred line CCMC of 'Changchun dense thorn *Cucumis sativus*' and extremely downy mildew-susceptible RIL individuals by the InDel marker 17ID185, while single bands with the same size of 100 bp were amplified out of 'IL52' and extremely downy mildew-resistant RIL individuals. (FIG. 3).

The recombinant individuals RIL114 which have high downy mildew resistance and accord with the aforementioned genotype were selected to be backcrossed with the high-generation inbred line CCMC of 'Changchun dense thorn *Cucumis sativus*', and from the first backcrossed generation, the individuals RIL114-BC1 in which the dm5.2 region was heterozygous and the other chromosome regions approximated the banding pattern of the high-generation inbred line CCMC of 'Changchun dense thorn *Cucumis sativus*' continued to be selected to be backcrossed with the high-generation inbred line CCMC of 'Changchun dense thorn *Cucumis sativus*'; after backcrossing for two generations, the individuals in which the dm5.2 region were heterozygous and the other chromosome regions were almost the banding pattern of the high-generation inbred line CCMC of 'Changchun dense thorn *Cucumis sativus*' were selected for selfing, the individuals RIL114-BC2 in which the dm5.2 region were heterozygous were selected for selfing, and ultimately, the individuals DMR114 in which the genotype in the dm5.2 region coincided with the banding pattern of 'IL52' and the other chromosome regions were the banding pattern of the high-generation inbred line of 'Changchun dense thorn *Cucumis sativus*' were obtained.

3. Characteristics of New Downy Mildew-Resistant Interspecific Hybrid *Cucumis sativus* Variety DMR114:

DMR114 basically has the traits of North China type 'Changchun dense thorn *Cucumis sativus*', as well as downy mildew resistance, and is an inbred line.

DMR114 is a asubgynoecious, the growth of plants is vigorous, the internode length is 10 cm to 12.5 cm, the stem diameter is 0.6 cm to 0.75 cm, leaves are green, the average maximum leaf area is 23 cm*22 cm, first female flower nodes are seventh to eleventh nodes, a female flower emerges at each following node, commercial *Cucumis sativus* is linear and green with a large number of white thorns, the average *Cucumis sativus* length is 22 cm to 26 cm, the average *Cucumis sativus* diameter is 3 cm to 4 cm, and both main and lateral bines bear *Cucumis sativus*.

4. Application of New Downy Mildew-Resistant Interspecific Hybrid *Cucumis sativus* Variety DMR114:

DMR114 and an ordinarily cultivated *Cucumis sativus* with high combining ability were planted according to 3:1, and routine plant management was carried out. Bagging treatment was performed at the flowering stage to prevent pollen contamination, and with DMR114 as a female parent and the ordinarily cultivated *Cucumis sativus* as a male parent, artificial pollination was performed. Mature fruits on the DMR114 plants were harvested, the *Cucumis sativus* was cut open, the seeds were washed and sun-dried, thereby downy mildew-resistant first-generation hybrid seeds were obtained.

What is claimed is:

1. A breeding method for a new downy mildew-resistant interspecific hybrid Cucumis sativus variety, wherein the breeding method comprises the following steps:

(1) performing hybridization with the high-generation inbred line CCMC of 'Changchun dense thorn *Cucumis sativus*' as a female parent and a *Cucumis sativus-Cucumis hystrix* introgression line material 'IL52' as a male parent to obtain hybrid F1 plants, selfing the hybrid F1 plants to obtain F2 plants, and continuously constructing an F6 recombinant inbred line by the single seed descent method; and identifying of phenotypes of the recombinant inbred line populations during the natural inoculation of downy mildew at the adult plant stage in the field for 4 years, and screening for recombinant individuals with high resistance and good fruit marketability;

(2) backcrossing and molecular marker-assisted selection utilizing three InDel markers closely linked with the downy mildew-resistant major effect QTLdm5.2 to proceed with genotype screening from the high downy mildew-resistant individuals, and selecting individuals in which the dm5.2 region is heterozygous and the other chromosome regions approximate the banding pattern of the high-generation inbred line CCMC of 'Changchun dense thorn *Cucumis sativus*', wherein the primers of the three InDel markers closely linked with the downy mildew-resistant major effect QTLdm5.2 are respectively: 17ID76-F: SEQ ID NO. 1/17ID76-R: SEQ ID NO. 2; 17ID129-F: SEQ ID NO. 3/17ID129-R: SEQ ID NO. 4; 17ID185-F: SEQ ID NO. 5/17ID185-R: SEQ ID NO. 6; and selecting the recombinant individuals having high downy mildew resistance and the aforementioned genotype to perform backcrossing with the high-generation inbred line CCMC of 'Changchun dense thorn *Cucumis sativus*', and continuously selecting from the first backcrossed generation the individuals in which the dm5.2 region is heterozygous and the other chromosome regions approximate the banding pattern of the high-generation inbred line CCMC of 'Changchun dense thorn *Cucumis sativus*' to perform backcrossing with the high-generation inbred line CCMC of 'Changchun dense thorn *Cucumis sativus*'; after backcrossing for two generations, selecting the individuals in which the dm5.2 region is heterozygous and the other chromosome regions are almost the banding pattern of the high-generation inbred line CCMC of 'Changchun dense thorn *Cucumis sativus*' for selfing, selecting the individuals in which the dm5.2 region is heterozygous for selfing, and ultimately, obtaining the individuals in which the genotype in the dm5.2 region coincides with the banding pattern of 'IL52' and the other chromosome regions are the banding pattern of the high-generation inbred line CCMC of 'Changchun dense thorn *Cucumis sativus*' to provide the new downy mildew-resistant interspecific hybrid Cucumis sativus variety.

2. The breeding method for the new downy mildew-resistant interspecific hybrid *Cucumis sativus* variety according to claim 1, wherein the new downy mildew-resistant interspecific hybrid *Cucumis sativus* variety has the following characteristics:

the new downy mildew-resistant interspecific hybrid *Cucumis sativus* variety has the traits of the high-generation inbred line CCMC of North China type 'Changchun dense thorn *Cucumis sativus*' on the whole, as well as downy mildew resistance, and is an inbred line;

the new downy mildew-resistant interspecific hybrid *Cucumis sativus* variety is a subgynoecious, the growth of plants is vigorous, the internode length is 10 cm to 12.5 cm, the stem diameter is 0.6 cm to 0.75 cm, leaves are green, the average maximum leaf area is 23 cm*22 cm, first female flower nodes are at the seventh to eleventh nodes, a female flower emerges at each following node, commercial *Cucumis sativus* is linear and green with a large number of white thorns, the average *Cucumis sativus* length is 22 cm to 26 cm, the average *Cucumis sativus* diameter is 3 cm to 4 cm, and both main and lateral bines bear *Cucumis sativus*.

3. The breeding method for the new downy mildew-resistant interspecific hybrid *Cucumis sativus* variety according to claim 1, wherein genotype screening described in step (2) is to utilize the primers of the three InDel markers closely linked with the downy mildew-resistant major effect QTLdm5.2 to carry out PCR amplification for the genomic DNA of the high-resistance individuals screened out, and the amplification product undergoes electrophoresis on 6% non-denaturing polyacrylamide gel; single bands with the same size of 107 bp are amplified out of the high-generation inbred line CCMC of 'Changchun dense thorn *Cucumis sativus*' and extremely downy mildew-susceptible RIL individuals by the InDel marker 17ID76, while single bands with the same size of 114 bp are amplified out of 'IL52' and extremely downy mildew-resistant RIL individuals; single bands with the same size of 155 bp are amplified out of the high-generation inbred line CCMC of 'Changchun dense thorn *Cucumis sativus*' and extremely downy mildew-susceptible RIL individuals by the InDel marker 17ID129, while single bands with the same size of 148 bp are amplified out of 'IL52' and extremely downy mildew-resistant RIL individuals; and single bands with the same size of 97 bp are amplified out of the high-generation inbred line CCMC of 'Changchun dense thorn *Cucumis sativus*' and extremely downy mildew-susceptible RIL individuals by the InDel marker 17ID185, while single bands with the same size of 100 bp are amplified out of 'IL52' and extremely downy mildew-resistant RIL individuals.

4. The breeding method for the new downy mildew-resistant interspecific hybrid *Cucumis sativus* variety according to claim 1, wherein the composition of aPCR amplification reaction system is as follows: 10.0 µL of 2×Taq Master Mix, 4.0µL of ddH$_2$O, 2.0 µL of forward primer, 2.0 µL of reverse primer, 2.0 µL of DNA (10 ng/uL), and 20 µL of total reaction volume, and where the reaction procedure is: 5 min of pre-denaturation under 94° C.; 30 s of pre-denaturation under 94° C. in each cycle, 30 s of annealing under 55° C., 1 min of extension under 72° C., and 35 cycles in total; 10 min of extension under 72° C., and storage under 4° C.

5. A method of breeding downy mildew-resistant interspecific hybrid *Cucumis sativus* variety comprising planting the new downy mildew-resistant interspecific hybrid *Cucumis sativus* variety bred by the breeding method according to claim 1 and an ordinarily cultivated *Cucumis sativus* with high combining ability and after routine plant management, bagging treatment is performed at the flowering stage to prevent pollen contamination, and performing certified pollination with the new downy mildew-resistant interspecific hybrid *Cucumis sativus* variety as a female parent and the ordinarily cultivated *Cucumis sativus* as a male parent.

* * * * *